US010222371B1

(12) United States Patent
Hacker

(10) Patent No.: US 10,222,371 B1
(45) Date of Patent: *Mar. 5, 2019

(54) LATERAL FLOW ASSAY CONTAINED WITHIN A BIOPSY SPECIMEN COLLECTION BOTTLE FOR QUALITATIVE VISUAL DETECTION OF PROTEIN PRESENT IN BIOPSY SAMPLES

(71) Applicant: Nano 2.0 Business Press, LLC, Delray Beach, FL (US)

(72) Inventor: Steven M. Hacker, Delray Beach, FL (US)

(73) Assignee: Nano 2.0 Business Press, LLC, Delray Beach, FL (US)

( * ) Notice: Subject to any disclaimer, the term of this patent is extended or adjusted under 35 U.S.C. 154(b) by 360 days.

This patent is subject to a terminal disclaimer.

(21) Appl. No.: 15/188,530

(22) Filed: Jun. 21, 2016

(51) Int. Cl.
| | |
|---|---|
| *G01N 33/543* | (2006.01) |
| *G01N 33/558* | (2006.01) |
| *G01N 21/78* | (2006.01) |
| *B01L 3/00* | (2006.01) |
| *G01N 21/77* | (2006.01) |
| *G01N 21/75* | (2006.01) |

(52) U.S. Cl.
CPC ......... *G01N 33/558* (2013.01); *B01L 3/5023* (2013.01); *G01N 21/78* (2013.01); *G01N 33/54366* (2013.01); *B01L 2300/041* (2013.01); *B01L 2300/0609* (2013.01); *B01L 2300/0803* (2013.01); *B01L 2300/0832* (2013.01); *B01L 2300/0887* (2013.01); *B01L 2300/165* (2013.01); *G01N 2021/757* (2013.01); *G01N 2021/7763* (2013.01)

(58) Field of Classification Search
None
See application file for complete search history.

(56) References Cited

U.S. PATENT DOCUMENTS

| 5,119,830 | A  | * | 6/1992 | Davis | B01L 3/502 |
| | | | | | 422/568 |
| 7,041,253 | B1 | * | 5/2006 | Sun | A61B 10/007 |
| | | | | | 422/408 |
| 2002/0085953 | A1 | * | 7/2002 | Parker | A61B 10/007 |
| | | | | | 422/412 |
| 2007/0259442 | A1 | * | 11/2007 | Gould | A61B 10/007 |
| | | | | | 436/165 |
| 2007/0275475 | A1 | * | 11/2007 | Liang | B01L 3/502 |
| | | | | | 436/165 |

\* cited by examiner

*Primary Examiner* — Changhwa J Cheu
(74) *Attorney, Agent, or Firm* — Nancy J. Flint, Attorney at Law, P.A.; Nancy J. Flint, Esq.

(57) ABSTRACT

A qualitative detection system and method for visual verification of the presence of human protein in a biopsy specimen collection bottle is disclosed. The system comprises a lateral flow assay assembly securely contained within the lid of a biopsy specimen collection bottle or secured at the bottom of the bottle. The lateral flow assay assembly comprises components that amplify in color intensity through a chromogenic reaction in the presence of certain proteins. A change in color of the components of the lateral flow assay assembly acts as a visual index to qualitatively confirm the placement of human tissue in the biopsy specimen collection bottle.

20 Claims, 5 Drawing Sheets

LATERAL FLOW ASSAY CONTAINED WITHIN A BIOPSY SPECIMEN COLLECTION BOTTLE FOR QUALITATIVE VISUAL DETECTION OF PROTEIN PRESENT IN BIOPSY SAMPLES

FIELD OF THE INVENTION

The invention relates to a qualitative detection system and method for visual verification of the presence of human protein in a biopsy specimen collection bottle. The system comprises a lateral flow assay assembly comprising components that amplify in color intensity through a chromogenic reaction in the presence of certain proteins. A change in color of the components of the lateral flow assay assembly acts as a visual index to qualitatively confirm the placement of human tissue in the biopsy specimen collection bottle. The lateral flow assay assembly may be securely contained within the lid of the biopsy specimen collection bottle, or it may be secured at the bottom of the biopsy specimen collection bottle.

BACKGROUND OF THE INVENTION

It is common practice for physicians and surgeons after removing human tissue from the body to place such tissue in a biopsy specimen collection bottle containing fixative to enable processing of the tissue so that a pathologist may render a diagnosis of the tissue. During the rush of surgery or rapid pace outpatient and inpatient biopsies, the surgeon may forget to place the tissue into the biopsy specimen collection bottle, unknowingly lose the specimen, or small specimens may be accidentally disposed of after they are thought to have been placed into a biopsy specimen collection bottle. Further, the physician or surgical team may not carefully examine the biopsy specimen collection bottle to ensure and confirm that staff had placed the specimen in the tissue collection bottle or the submitted specimen is so small it may be difficult to visualize its presence in the biopsy specimen collection bottle. As a result, the pathology labs, not infrequently, receive a biopsy specimen collection bottle with no tissue inside.

Reference is made to U.S. Pat. No. 9,091,682, wherein a verification method for confirming the presence of tissue in a specimen bottle utilizing a chromogenic test pad consisting of absorbent paper, and a test pad comprised of a guaiac compound and peroxygen compound is disclosed. The use of a chromogenic test pad comprising guaiac compound and a peroxygen compound as disclosed therein limits the tissue types available for testing and also may confuse an observer as the presence of blood may not be indicative of the presence of other proteins found in other tissue.

U.S. Pat. Nos. 4,725,553; 2,838,377; 3,996,006; and 4,175,923 disclose various tests for detecting occult blood in stool using guaiac paper or guaiac substitutes and or various activating substances.

BRIEF SUMMARY OF THE INVENTION

The invention relates to a lateral flow assay assembly secured within a biopsy specimen collection bottle which undergoes a chromogenic reaction confirming the presence of human protein in the biopsy specimen collection bottle. More specifically, in one embodiment the device comprises a lateral flow assay assembly secured in the undersurface of a lid of a biopsy specimen collection bottle that amplifies the presence of trace amounts of protein. In one embodiment, the device comprises a lateral flow assay assembly secured at the bottom of a biopsy specimen collection bottle that amplifies the presence of trace amounts of protein. The lateral flow assay assembly thus provides a qualitative visual index of the placement of protein in the biopsy specimen collection bottle. The lateral flow assay assembly comprises a variety of known chromogenic substances that effect a color change in the presence of human protein; a protein binding disc such as a nitrocellulose membrane; an adsorbent sink pad; an application chemistry pad; a hydrophobic film; and a hydrophobic film spacer.

BRIEF DESCRIPTION OF THE DRAWINGS

The various features of the present invention and the manner of attaining them will be described in greater detail with reference to the following description, claims, drawings, wherein like designations denote like elements.

DETAILED DESCRIPTION OF THE INVENTION

Figure 1A:
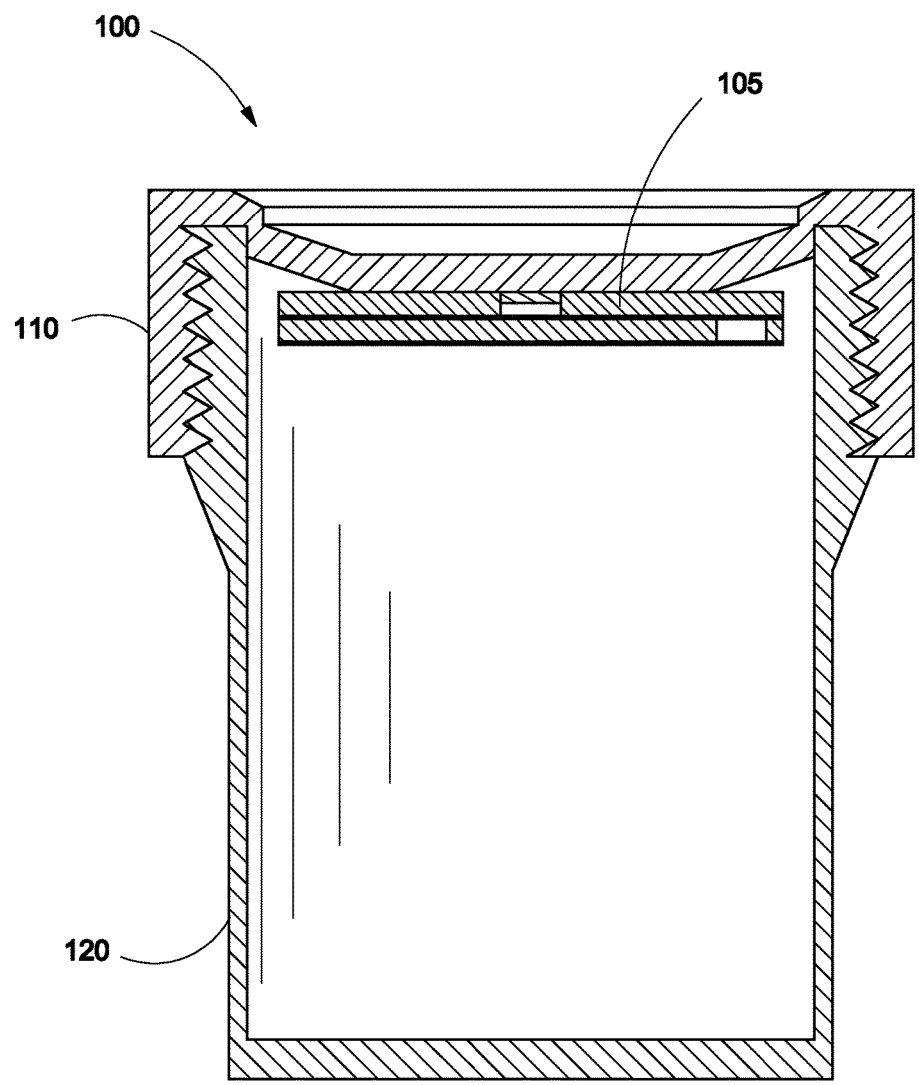
FIG. 1A depicts an assembled cross sectional view of the lid of a biopsy specimen collection bottle with a lateral flow assay assembly disposed on the undersurface of the lid according to one embodiment of the invention.

Referring to FIG. 1A, a biopsy specimen collection bottle with lateral flow assay assembly 100 is shown. Lateral flow assay assembly 105 securely fits into the undersurface of the lid 110 of a biopsy specimen collection bottle 120. Lateral flow assay assembly 105 may be attached to the undersurface of the lid 110 by any type of adhesive, bonding or glue that is not affected by formalin.

Figure 1B:
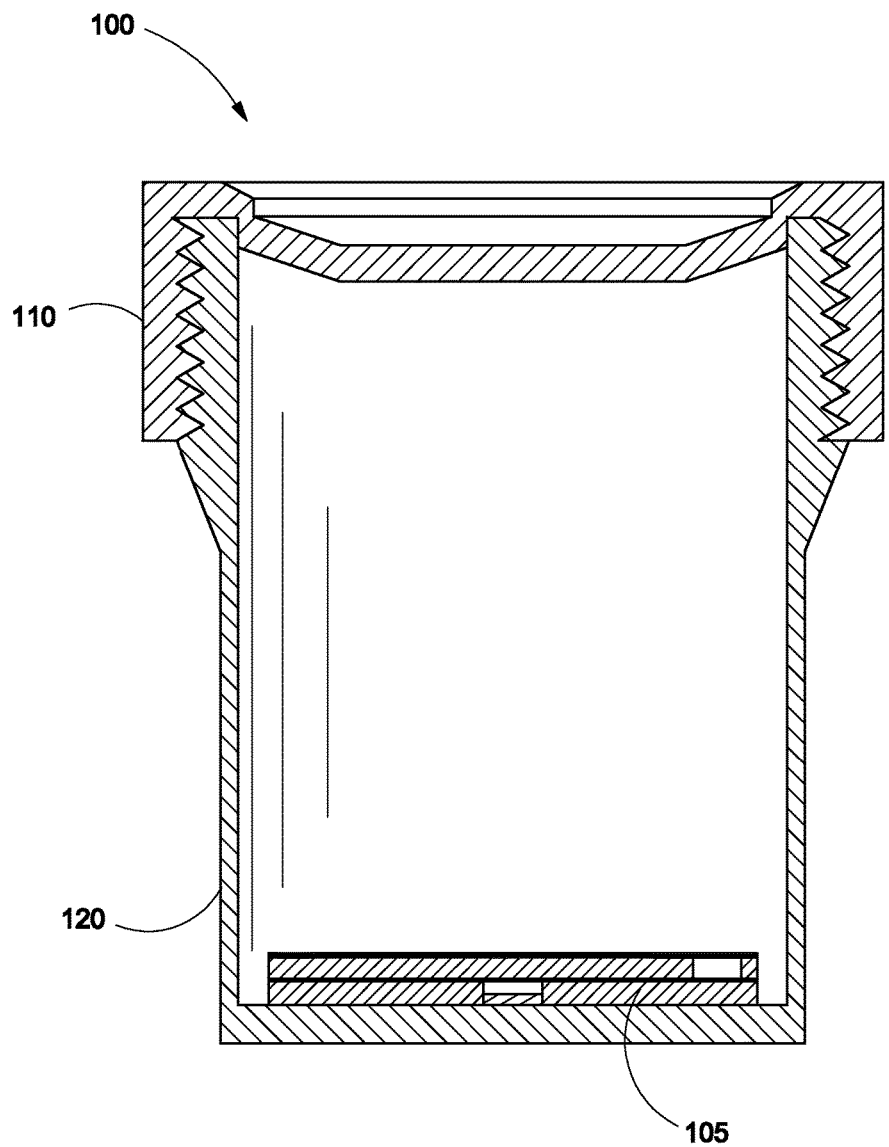
FIG. 1B depicts an assembled cross sectional view of the lid of a biopsy specimen collection bottle with a lateral flow assay assembly disposed at the bottom of the bottle according to one embodiment of the invention.

Referring to FIG. 1B, a biopsy specimen collection bottle with lateral flow assay assembly 105 is shown. Lateral flow assay assembly 105 securely fits on the bottom 180 of a biopsy specimen collection bottle 120. Lateral flow assay assembly 105 may be attached to the bottom 180 of the biopsy specimen collection bottle 120 by any type of adhesive, bonding or glue that is not affected by formalin.

Figure 2A:
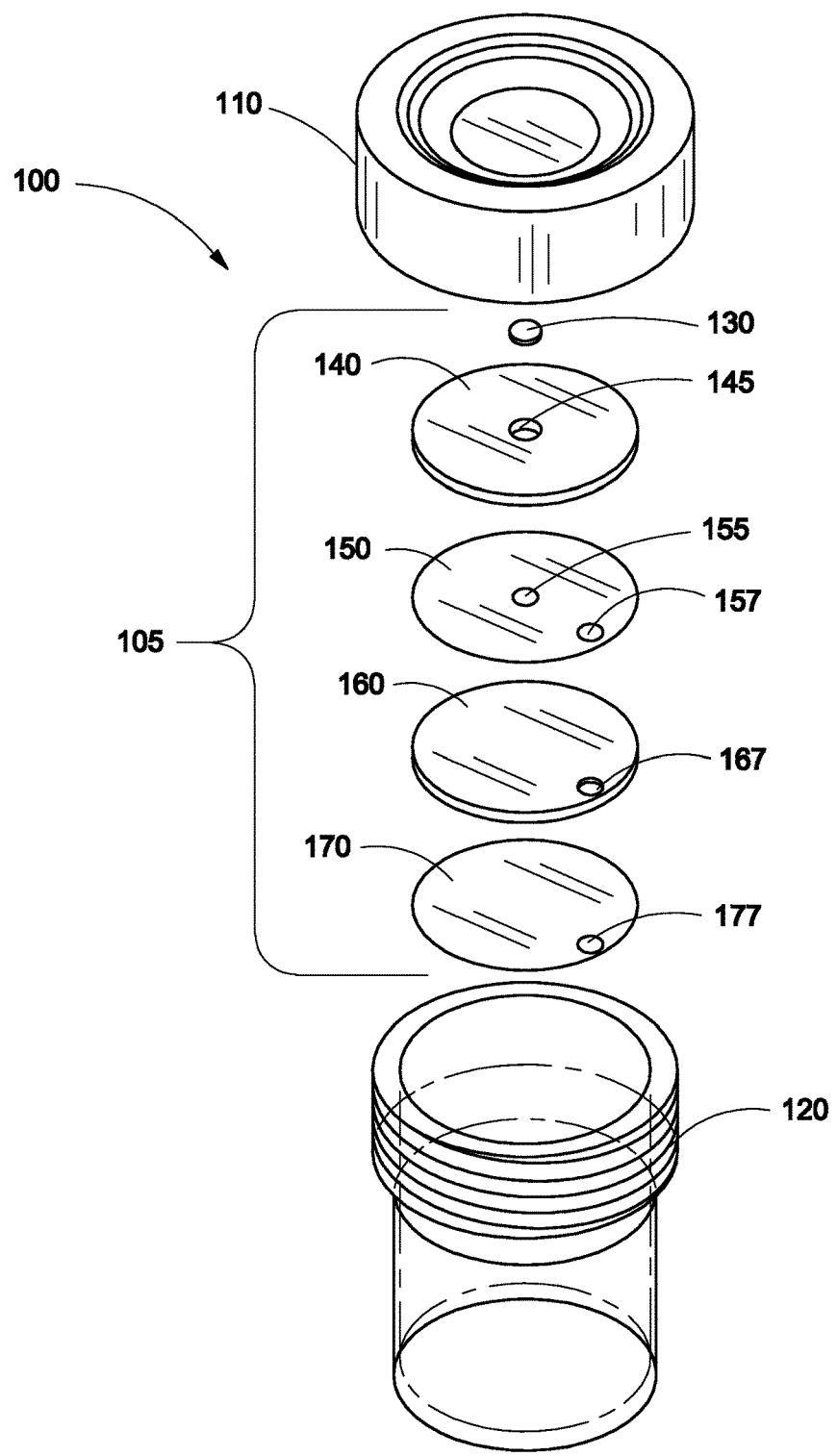
FIG. 2A depicts an exploded view of the lid of a biopsy specimen collection bottle with a lateral flow assay assembly disposed on the undersurface of the lid according to one embodiment of the invention.

Referring to FIG. 2A, biopsy specimen collection bottle with lateral flow assay assembly 100 is shown in exploded view. Lateral flow assay assembly 105 comprises, in order from the side adjacent the undersurface of lid 110 of biopsy specimen collection bottle 120, a nitrocellulose membrane 130; an application chemistry pad 140 having a space therethrough 145 that engages with nitrocellulose membrane 130; a hydrophobic spacer film 150 having a space 155 therethrough aligning with space 145 in application chemistry pad 140 and a port 157 therethrough; an adsorbent sink pad layer 160 having a port 167 therethrough; a hydrophobic film layer 170 having a port 177 therethrough. The components making up the lateral flow assembly 105 may be attached to each other by any type of adhesive, bonding or glue that is not affected by formalin.

Figure 2B:
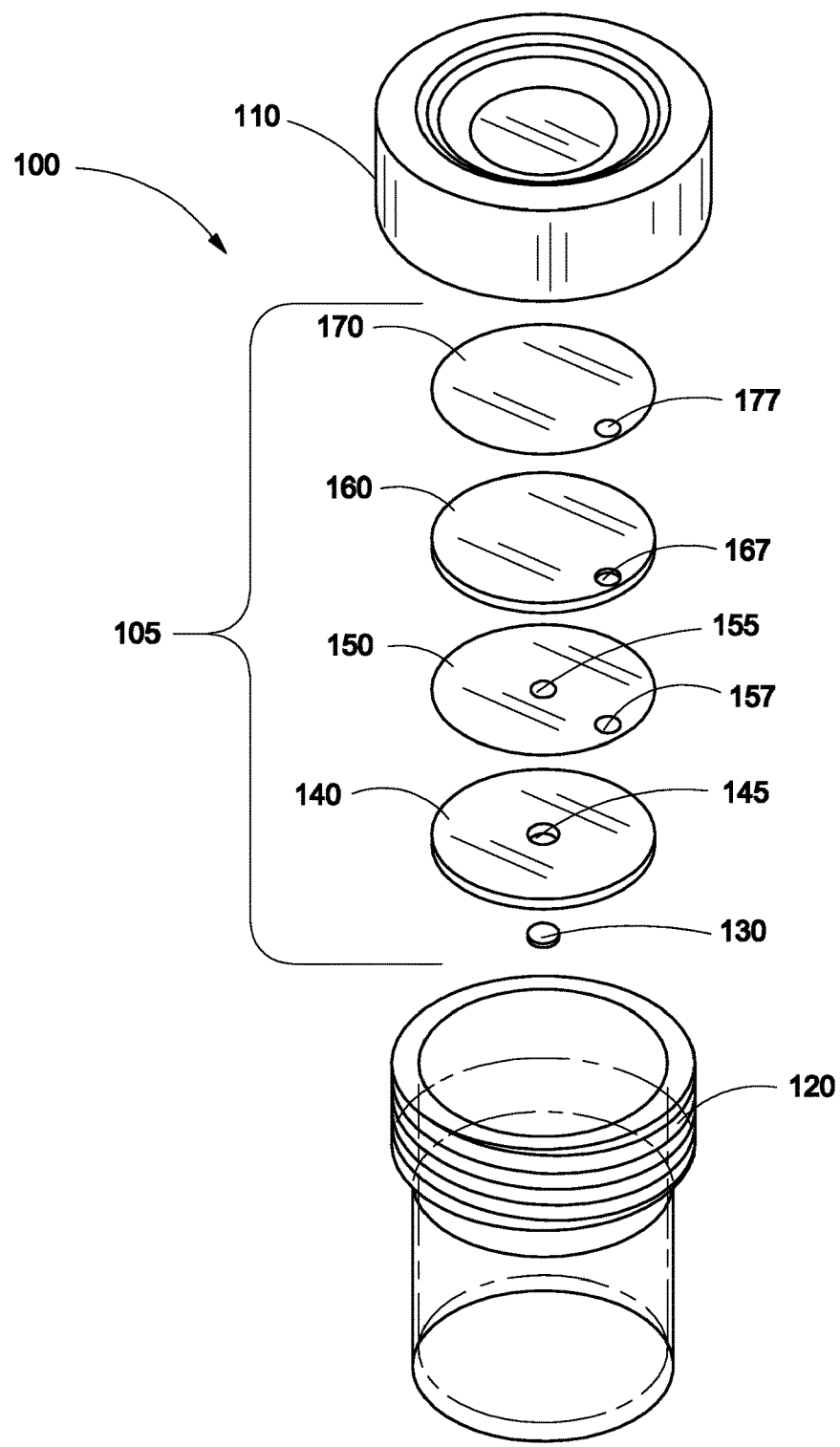
FIG. 2B depicts an exploded view of the lid of a biopsy specimen collection bottle with a lateral flow assay assembly disposed at the bottom of the bottle according to one embodiment of the invention.

Referring to FIG. 2B, biopsy specimen collection bottle with lateral flow assay assembly 100 is shown in exploded view. Lateral flow assay assembly 100 comprises, in order from the side adjacent the interior of the biopsy specimen collection bottle 120, a hydrophobic film layer 170 having a port 177 therethrough; an adsorbent sink pad layer 160 having a port 167 therethrough; a hydrophobic spacer film 150 having a space 155 therethrough aligning with space 145 in application chemistry pad 140 and a port 157 therethrough; an application chemistry pad 140 having a space therethrough 145; and a nitrocellulose membrane 130; that engages with space 145. The components making up the lateral flow assembly 105 may be attached to each other by any type of adhesive, bonding or glue that is not affected by formalin.

Figure 3:
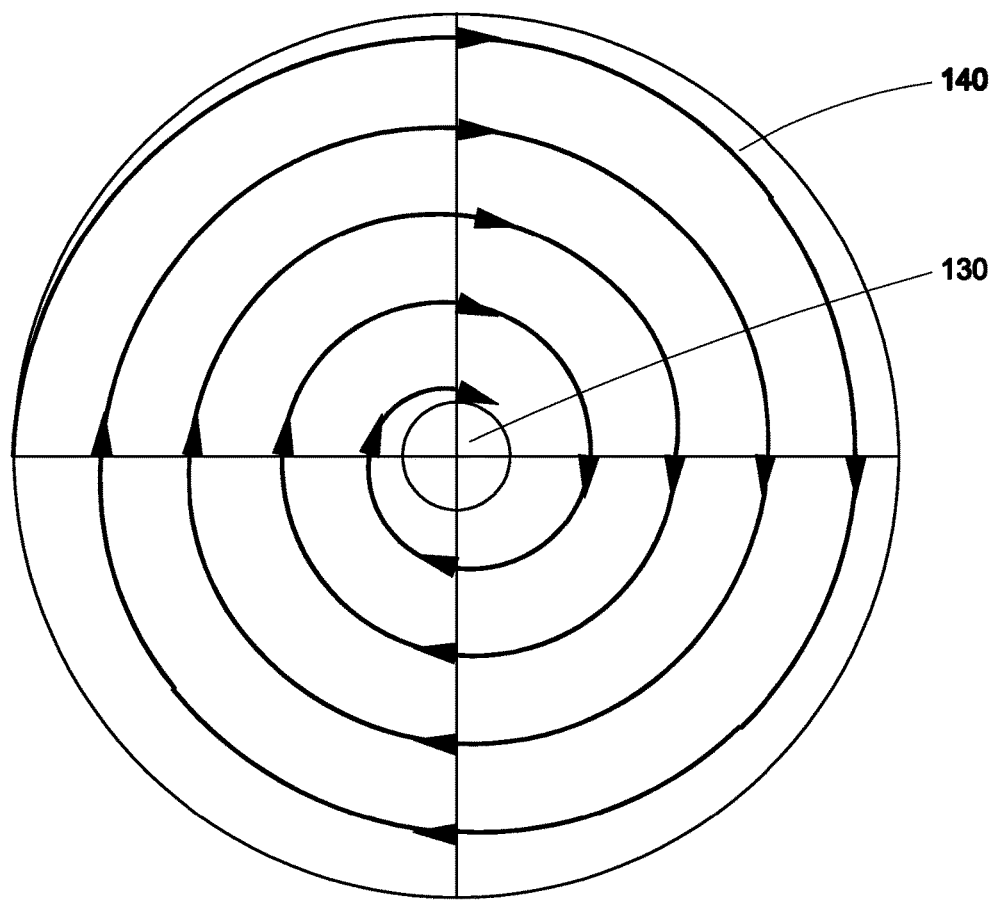
FIG. 3 provides an isometric top view showing the flow pattern of fluid on a lateral flow assay assembly according to one embodiment of the invention.

Referring to FIG. 3, a cross sectional top view is shown of application chemistry pad 140 with arrows showing direction of capillary action. The capillary action drives fluid around a spiral channel formed in the application chemistry pad 140, which contains reagents and dyes for qualitative protein assay. Fluid flows around the application chemistry pad 140 in the direction of the arrows towards the center of the application chemistry pad 140 and then through nitrocellulose membrane 130 engaged in space 145 in the center of application chemistry pad 140. Protein present in the fluid binds and concentrates on nitrocellulose membrane 130, amplifying the color intensity of the assay.

The method of the invention for the embodiment having lateral flow assay assembly 100 securely fitted into the undersurface of the lid 110 is as follows. Application chemistry pad 140 is securely fitted into the undersurface of lid 110 of biopsy specimen collection bottle 120. A specimen and a fixative solution, such as formalin solution, is placed into biopsy specimen collection bottle 120. When biopsy specimen collection bottle 120 is inverted, the buffer solution contacts hydrophobic film layer 170. The buffer solution flows through port 177 to adsorbent sink pad layer 160, then flows through port 167 through to hydrophobic spacer film 150, passing through port 157 to then contact application chemistry pad 140. Application chemistry pad 140 is impregnated with chromogenic substances that effect a color change in the presence of human protein. Protein in the fluid binds to nitrocellulose membrane 130. Contact of proteins in the fluid with application chemistry pad 140 and its chromogenic substances followed by binding in nitrocellulose membrane 130 provides a qualitative visual index that protein is present in the fluid in biopsy specimen collection bottle 120.

For the embodiment having lateral flow assay assembly secured to the bottom of the bottle 120, the sequence is identical except that the user observes the bottom of the bottle to look for a color change.

Suitable chromogenic substances that can be used in the invention include but are not limited to Coomassie Brilliant Blue, Coomassisie R-250 (Red) and G-250 dyes green (colloidal coomassie dyes), Coomassie, fluorescent, silver, and negative stains, Whatman cellulose chromatography paper and Pierce BCA 660 nm (polyhydroxybenzenesulfonephthalein-type dye).

Some suitable chromogenic substances require one or more activating substances while other suitable chromogenic substances may not require one or more activating substances. Persons skilled in the art can determine appropriate chromogenic substances and whether they require activating substances. Activating substances that can be used in the invention include but are not limited to acid buffering solutions such as BSA lyophilized powder, acetic acid, phosphoric acid and methanol/acetic acid/water mixture. Under certain conditions, such as a test pad or ingredient in the bottle, may require the addition of activating solution(s) to the biopsy specimen collection bottle to effect a color change.

While the invention has been particularly shown and described in reference to the certain embodiments, persons skilled in the art will recognize that various changes in form and detail may be made without departing from the scope and spirit of the invention. Although the embodiments have been described in reference to a lateral flow assay assembly and biopsy specimen collection bottle, the assembly, system and method according to the embodiments of the present invention may also apply to any type of chromogenic test pad consisting of any type of chromogenic chemical reaction inserted into the lid or any portion of a collection bottle, that would enable the viewing of a chromogenic test pad through the bottom of a collection bottle to confirm the presence of a chromogenic color change to verify the presence of trace amounts of protein.

The scope of the invention also extends to various combinations and modifications that may fall within the spirit of the appended claims.

What is claimed is:

1. A visual verification method for confirming the presence of human protein in a sample comprising:
   a. providing a specimen bottle and a corresponding lid;
   b. securing a lateral flow assembly in the interior of the specimen bottle, the lateral flow assembly comprising one or more chromogenic substances;
   c. introducing a sample and a solution comprising a fixative into the interior of the specimen bottle;
   d. sealing the specimen bottle with the lid;
   e. thereafter contacting the sample and fixative solution in the interior of the specimen bottle containing the lateral flow assembly comprising the one or more chromogenic substances;
   f. observing whether a color change has occurred in the lateral flow assay assembly; and
   g. correlating a color change in the lateral flow assay assembly with the presence of protein in the sample in the interior of the specimen bottle; and
   h. correlating no color change in the lateral flow assay assembly with the absence of protein in the sample in the interior of the specimen bottle, wherein the lateral flow assay assembly comprises a protein binding disc in the center of an application chemistry pad, a hydrophobic spacer film, an absorbent sink pad, and a hydrophobic film layer, wherein the application chemistry pad, the hydrophobic spacer film, the absorbent sink pad, and the hydrophobic film layer each comprises a port allowing fluid to flow from the center of the application pad to adjacent pads and layers.

2. The method of claim 1 wherein the protein binding disc comprises a nitrocellulose membrane.

3. The method of claim 2, wherein the application chemistry pad comprises the one or more chromogenic substances.

4. The method of claim 3, wherein the one or more chromogenic substances comprise Coomassie Brilliant Blue, Coomassisie R-250 (Red) and G-250 dyes green (colloidal coomassie dyes), Coomassie, fluorescent, silver, and negative stains, Pierce BCA 660 nm (polyhydroxybenzenesulfonephthalein-type dye) and combinations thereof.

5. The method of claim 1, further comprising introducing one or more activation solutions into the interior of the specimen bottle along with the sample and the fixative solution.

6. The method of claim 5, wherein the one or more activation solutions comprise BSA lyophilized powder, acetic acid, phosphoric acid, methanol/acetic acid/water mixture and combinations thereof.

7. The method of claim 1 wherein the lateral flow assay assembly is secured within the undersurface of the lid of the specimen bottle.

8. The method of claim 1 wherein the lateral flow assay assembly is secured to the bottom of the interior of the specimen bottle.

9. The method of claim 1 wherein the specimen bottle comprises a clear specimen bottle.

10. The method of claim 1 wherein further the lateral flow assay changes color in the presence of protein.

11. A lateral flow assay assembly for detecting presence of protein in a sample, comprising:
a protein binding disc;
an application chemistry pad comprising a space in the center of the pad, wherein the protein binding disc is matingly engaged with the application chemistry pad within the space in the application chemistry pad;
an adsorbent sink pad;
a hydrophobic spacer film disposed between the application chemistry pad and the adsorbent sink pad; and
a hydrophobic film layer,
wherein the adsorbent sink pad, the hydrophobic spacer film and the hydrophobic film layer each comprises a port allowing fluid to flow from the center of the application chemistry pad to adjacent pads and layers.

12. The lateral flow assay assembly of claim 11, wherein the protein binding disc comprises a nitrocellulose membrane.

13. The lateral flow assay assembly of claim 12, wherein the application chemistry pad comprises one or more chromogenic substances.

14. The lateral flow assay assembly of claim 13, wherein the one or more chromogenic substances comprise Coomassie Brilliant Blue, Coomassisie R-250 (Red) and G-250 dyes green (colloidal coomassie dyes), Coomassie, fluorescent, silver, and negative stains, Pierce BCA 660 nm (polyhydroxybenzenesulfonephthalein-type dye) and combinations thereof.

15. A specimen bottle having a lateral flow assay assembly for detecting presence of protein in a sample, comprising:
a specimen bottle; and
a lateral flow assembly comprising:
a protein binding disc;
an application chemistry pad comprising a space in the center of the pad, wherein the protein binding disc is matingly engaged with the application chemistry pad within the space in the application chemistry pad;
an adsorbent sink pad;
a hydrophobic spacer film layer disposed between the application chemistry pad and the adsorbent sink pad; and
a hydrophobic film layer,
wherein the adsorbent sink pad, the hydrophobic spacer film and the hydrophobic film layer each comprise a port allowing fluid to flow from the center of the application chemistry pad to adjacent pads and layers.

16. The specimen bottle having a lateral flow assay assembly of claim 15, wherein the protein binding disc comprises a nitrocellulose membrane.

17. The specimen bottle having a lateral flow assay assembly of claim 16, wherein the application chemistry pad comprises one or more chromogenic substances.

18. The specimen bottle having a lateral flow assay assembly of claim 17, wherein the one or more chromogenic substances comprise Coomassie Brilliant Blue, Coomassisie R-250 (Red) and G-250 dyes green (colloidal coomassie dyes), Coomassie, fluorescent, silver, and negative stains, Pierce BCA 660 nm (polyhydroxybenzenesulfonephthalein-type dye) or combinations thereof.

19. The specimen bottle having a lateral flow assay assembly of claim 15 further comprising a lid, wherein the lateral flow assay assembly is secured to the undersurface of the lid.

20. The specimen bottle having a lateral flow assay assembly of claim 15, wherein the lateral flow assay assembly is secured to the bottom of the interior of the specimen bottle.

* * * * *